(12) United States Patent
Karr et al.

(10) Patent No.: US 9,216,005 B2
(45) Date of Patent: Dec. 22, 2015

(54) SYNCHRONIZED VIEW DATA ACQUISITION BETWEEN STATIONARY SPECTRAL DETECTORS AND ROTATING ENERGY INTEGRATING DETECTORS FOR SPECTRAL COMPUTER-AIDED TOMOGRAPHY

(71) Applicants: Kabushiki Kaisha Toshiba, Tokyo (JP); Toshiba Medical Systems Corporation, Otawara-shi (JP)

(72) Inventors: Alan Karr, Port Barrington, IL (US); Yu Zou, Naperville, IL (US); Yuexing Zhang, Naperville, IL (US); Hiroaki Miyazaki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 80 days.

(21) Appl. No.: 14/064,660

(22) Filed: Oct. 28, 2013

(65) Prior Publication Data

US 2015/0117591 A1    Apr. 30, 2015

(51) Int. Cl.
*A61B 6/00* (2006.01)
*A61B 6/03* (2006.01)

(52) U.S. Cl.
CPC . *A61B 6/54* (2013.01); *A61B 6/032* (2013.01); *A61B 6/467* (2013.01)

(58) Field of Classification Search
CPC ............ A61B 6/00; A61B 6/54; A61B 6/032; A61B 6/467; A61B 2562/0219; A61B 5/055; A61B 5/1102; A61B 5/113; A61B 5/7239; A61B 5/7285; A61B 5/07; A61N 2005/1087; A61N 2005/1061; A61N 2005/1059; A61N 5/1049; A61N 5/1067; A61N 5/10; H05H 13/04; H05H 7/04; H05H 7/08; H05H 7/10
USPC .................................................. 378/4, 15, 19
See application file for complete search history.

(56) References Cited

U.S. PATENT DOCUMENTS

| 5,692,507 A * | 12/1997 | Seppi et al. ................... 600/407 |
| 6,574,301 B1 * | 6/2003 | Jansen ............................. 378/20 |
| 8,798,350 B2 | 8/2014 | Zou |
| 2007/0005278 A1 * | 1/2007 | Brunnett ......................... 702/78 |
| 2009/0045859 A1 * | 2/2009 | Huffman et al. .............. 327/159 |
| 2014/0239715 A1 * | 8/2014 | Weedon et al. ................. 307/17 |

FOREIGN PATENT DOCUMENTS

JP    2013-192951    9/2013

* cited by examiner

*Primary Examiner* — Irakli Kiknadze
(74) *Attorney, Agent, or Firm* — Oblon, McClelland, Maier & Neustadt, L.L.P.

(57) ABSTRACT

A control circuit for a computer-aided tomography (CT) system includes an input that receives a master timing signal and an input that receives a first timing signal. The control circuit includes a mode detection circuit that determines the scan mode of the CT system based on the master timing signal and a first timing signal, where the frequency of the first time signal is lower than the frequency of the master timing signal. The control circuit also includes a circuit that generates a second timing signal based on the master timing signal and the scan mode, where the second timing signal that has a lower frequency than the master timing frequency but a higher frequency than the frequency of the first timing signal.

20 Claims, 6 Drawing Sheets

SYNCHRONIZED VIEW DATA ACQUISITION BETWEEN STATIONARY SPECTRAL DETECTORS AND ROTATING ENERGY INTEGRATING DETECTORS FOR SPECTRAL COMPUTER-AIDED TOMOGRAPHY

FIELD

Embodiments described herein generally relate to synchronization of computer-aided tomography (CT) systems for acquiring view data.

BACKGROUND

Evolution of computer-aided tomography (CT) systems is categorized in terms of "generations." For example, a third generation CT system includes one or more energy integrating detector(s) mounted at one side of a rotating gantry. One or more x-ray source(s) are mounted at an opposite side of the rotating gantry. The gantry rotates around a patient as the x-ray source emits x-rays, which are detected by the energy integrating detectors after passing through the patient. This detected energy is collected as view data and processed into CT images.

A fourth generation CT system includes photon-counting detectors arranged along a circle or portion of a circle (arc) that is centered on the patient. The photon counting detectors are fixed and do not rotate around the patient. Instead, a rotating x-ray source, which rotates about the patient, emits x-rays which are detected by the photon counting detectors in order to acquire view data that is then processed to form a CT image.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein.

DETAILED DESCRIPTION

Figure 1:
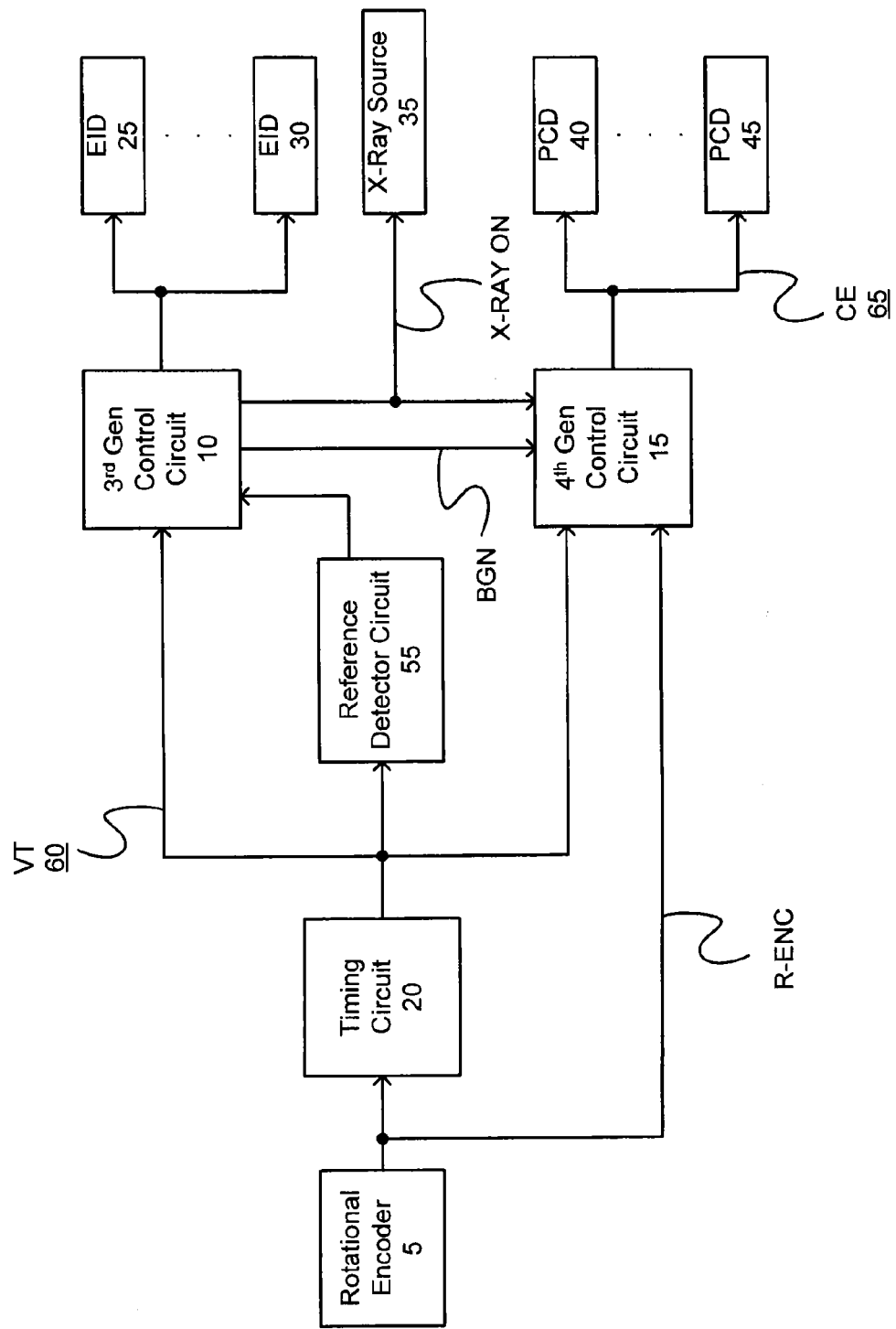
FIG. 1 is a block diagram of a CT system according to exemplary embodiments of the present disclosure.

In certain applications view data of a patient using both the third and the fourth generation CT systems is simultaneously acquired. In such a case synchronization of the two systems must be performed to avoid submitting the patient to two separate CT scans on two separate CT systems, and to avoid possible interference between the two systems.

According to one exemplary embodiment, a timing circuit for a computer-aided tomography (CT) system includes an input that receives a master timing signal and a mode detection circuit that determines the scan mode of the CT system based on the master timing signal and a first timing signal, where the frequency of the first time signal is lower than the frequency of the master timing signal. The timing circuit also includes a timing circuit that generates a second timing signal based on the master timing signal and the scan mode, where the second timing signal that has a lower frequency than the master timing frequency but a higher frequency than the frequency of the first timing signal.

According to the exemplary embodiment, the first timing signal, the second timing signal, and the master timing signal remain phase-locked irrespective of the scan mode.

In another exemplary embodiment, the timing circuit includes a first divider circuit that divides the master timing signal by a first predetermined value, a second divider circuit that divides the master timing signal by a second predetermined value, and a third divider circuit that divides the master timing signal by a third predetermined value. A multiplexer outputs an output of one of the first, second or third divider circuit based on the scan mode.

In a further exemplary embodiment, the scan mode detection circuit detects the scan mode based on a ratio of a period of the master timing signal to a period of the first timing signal.

In another exemplary embodiment, the period of the master timing signal is an integer multiple of the period of the first timing signal.

In a further exemplary embodiment, the timing circuit further includes a delay circuit that delays the output of the multiplexer by a predetermined time interval to generate the second timing signal.

In an additional exemplary embodiment, the master timing signal is generated as a rotational encoder signal of a rotational CT gantry by a rotational encoder circuit, the first timing signal is generated by an oscillator circuit and provided as a view trigger to a first CT subsystem, and the timing circuit provides the second timing signal as a count enable signal to a second CT subsystem.

In a further exemplary embodiment, a computer-aided tomography (CT) system includes a first CT subsystem including a gantry encoder that generates a rotational encoder signal based on rotation of a rotational gantry, and a control circuit that captures first CT images based on a view trigger signal that has a frequency lower than a frequency of the rotational encoder signal. A second CT subsystem includes a control circuit that captures second CT images based on a count enable signal, and a timing that determines a scan mode of the CT system based on a ration of a period of the rotational encoder signal to a period of the view trigger signal, and generates the count enable signal based on the rotational encoder signal and the scan mode, where the count enable signal has a frequency higher than the frequency of the view trigger signal and lower than the frequency of the rotational encoder signal.

In another exemplary embodiment, a method of synchronizing a computer-aided tomography system includes generating, in a rotational encoder, a rotational encoder signal based on rotation of a rotational gantry of a first CT subsystem, determining, in a scan mode detection circuit, a scan mode of the CT system based on the rotational encoder signal and a view trigger signal of the first CT subsystem, where the view trigger signal has a lower frequency than a frequency of the rotational encoder signal, capturing, in the first CT subsystem, first CT images based on the view trigger signal, generating, in the timing circuit, a count enable signal based on the rotational encoder signal and the scan mode, where the count enable signal having a frequency higher than the frequency of the view trigger signal and lower than a frequency of the rotational encoder signal; and capturing second CT images in a second CT subsystem based on the count enable signal.

In an even further exemplary embodiment, a non-transitory computer-readable medium is encoded with computer readable instructions that, when executed by a computer, cause the computer to perform a method that includes generating a rotational encoder signal based on rotation of a rotational gantry of a first CT subsystem, determining a scan mode of the CT system based on the rotational encoder signal and a view trigger signal of the first CT subsystem, where the view trigger signal has a lower frequency than a frequency of the rotational encoder signal, capturing first CT images based on the view trigger signal, generating a count enable signal based on the rotational encoder signal and the scan mode, where the count enable signal has a frequency higher than the frequency of the view trigger signal and lower than a frequency of the rotational encoder signal, and capturing second CT images based on the count enable signal.

Referring now to the drawings, wherein like reference numerals designate identical or corresponding parts throughout the several views. FIG. 1 is a block diagram of a CT system according to exemplary aspects of the present disclosure. In FIG. 1, the CT system includes both a third generation CT subsystem and fourth generation CT subsystem.

The third generation CT subsystem includes at least one x-ray source 35 that is connected to and controlled by the third generation control circuit 10. A plurality of energy integrating detectors, or EIDs, 25 to 35 are also connected to the third generation control circuit 10 in order to capture the x-ray energy that is emitted by the x-ray source 35 and which passes through a test subject (not shown) situated between the x-ray source 35 and the EIDs 25-30. In FIG. 1, only two EIDs 25, 30 are shown. However, the third generation CT subsystem of FIG. 3 may include any number of EIDs without departing from the scope of the present disclosure. The third generation CT subsystem may also include multiple x-ray sources 35, as can be appreciated.

The third generation control circuit 10 controls emission and detection of x-rays by the x-ray source 35 and the EIDs 25-30, respectively, through the signal X-RAY ON, and processes the detection data to form CT image data. As such, the third generation control circuit 10 may include a combination of digital control logic and analog electronics in order to perform these functions. For example, the third generation control circuit 10 may include at least one processor, such as a Core i5 or a Core i7 processor from Intel Corp., or FX, Phenom II, Athlon II or Sempron processors from AMD Corp, running an operating system such as Windows 7, MAC OS X, Linux, Unix or DOS, or a custom operating system written specifically for CT applications. The processor may also be a reduced instruction set processor (RISC), such as an ARM Cortex A8, or a specialized processor such as digital signal processor or microcontroller. The processing and control functions of the third generation control circuit 10 may also be implemented using discrete logic gates, in an application specific integrated circuit (ASIC) or in a field programmable gate array (FPGA). As can be appreciated, a combination of these devices may also be used to implement the control functions of the third generation CT system.

The third generation control circuit 10 also includes analog circuits such as filters, amplifiers, phase-locked loops, etc., in order to cause the x-ray source 35 to emit x-rays and to condition the signals received from the EIDs 25-30. The third generation control circuit 10 may also include electronic memory circuits, such as dynamic and/or static random access memory (SRAM, DRAM) to store collected data, programming instructions, control data and the like, and may also include read only memory (ROM) such as erasable read only memory (EPROM), electrically erasable read only memory (EEPROM) and flash memory to store computer-readable instruction code and other data to perform the functions of the third generation CT system. Input and output devices, such as a keyboard, mouse, monitor, Ethernet port, universal serial bus (USB) port, and the like may also be included.

The third generation control circuit 10 may be embodied, at least in part, as a desktop computer, laptop computer or tablet computer, or may form part of a CT device. The third generation control circuit 10 may also be distributed among a plurality of devices (i.e., computers, servers, etc.) that are interconnected by a wired network, such as an Ethernet network, or a wireless network, such as Bluetooth, Wi-Fi, cellular networks, and the like. In a distributed application, the components of the third generation control circuit 10 may even be interconnected by the internet. Thus, the particular implementation of the third generation control circuit 10 in no way limits the present disclosure.

In the third generation CT subsystem of FIG. 1, the EIDs 25-30 and the x-ray source 35 are mounted on opposite ends of a rotating gantry (not shown) so that the x-ray source 35 faces the EIDs 25-30. The gantry rotates about a central axis to which the test subject is aligned so that the EIDs 25-30 and the x-ray source 35 revolve around the test subject. A rotational encoder 5 tracks rotation of the gantry and outputs a corresponding rotational encoder signal. The rotational encoder may encode the rotation of the gantry using magnetic, light or other sensors, or combinations thereof, without departing from the scope of the present disclosure.

The rotational encoder 5 is connected to a timing circuit 20, which generates a view trigger signal (VT) 60 from the signal R-ENC of the rotational encoder 5. The timing circuit 20 then provides the VT signal 60 to the third generation control circuit 10 in order to capture CT image data. The VT signal 60 generated by the timing circuit 20 is generated at a predetermined, fixed frequency, such as one having a period of 833 micro-seconds. Of course, the VT signal 60 may also be generated at frequencies having periods other than 833 micro-seconds and may also be variable, as can be appreciated. Once generated, the timing circuit 20 also provides the VT signal 60 to a reference detector circuit 55 that detects a reference voltage used to normalize the CT data collected from the EIDs 25-30, and to the fourth generation control circuit 15, which is described below in detail.

A fourth generation CT subsystem includes photon count detectors (PCD) 40-45 and the fourth generation control circuit 15. The PCDs 40-45 are arranged along an arc whose vertex is located at the test subject, and are fixed in place. The PCDs 40-45 do not move during the CT imaging. Instead, the x-ray source 35 rotates around the test subject during CT imaging. The center of this rotation is the same as the vertex of the arc along which the PCDs 40-45 are arranged. The distance between the x-ray source 35 and the test subject does not have to be the same as the distance from the test subject to the PCDs 40-55, however. The x-ray source 35 may be closer to or further away from the test subject that the PCDs 40-55 without departing from the scope of the present disclosure.

The fourth generation control circuit 15 includes both the analog and digital electronics used to cause the PCDs to detect photons from those x-rays emitted by the x-ray source 35 in order to produce CT image data. The fourth generation control circuit may also include discrete logic circuits and/or ASIC, FPGA or specialized processors, such as a DSP processor, to capture and process the signals from the PCDs 40-45. As can be appreciated, analog circuits such as amplifiers and filters may also be included in order to condition the various signals provided to and received from the PCDs 40-45. The fourth generation control circuit may also include a display device, such as an LCD display or a cathode ray tube (CRT), a keyboard, touch screen, mouse or other known input device. The fourth generation control circuit 15 may also be implemented as a desktop, laptop, tablet or server computer or as a specialized circuit integrated into the CT device, or may be distributed among several of these devices and interconnected by wired and/or wireless networks, such as Ethernet, Bluetooth, Wi-fi, cellular networks or the internet.

The fourth generation control circuit 15 generates a count enable (CE) 65 signal, a described below in order to determine when to enable the PCDs 40-45 to detect photons from the x-ray source 35.

In operation, the x-ray source 35 of the third generation CT subsystem is located at a fan vertex of a fan of x-rays, and the EIDs 25-30 detect and measure the corresponding ray-sums at the same time in order to generate a source view or S-view. In the fourth generation CT subsystem, each PCD is at the fan vertex of the x-rays emitted by the x-ray source 35 as the x-ray source 35 sweeps around in an orbital trajectory. Thus, in the fourth generation CT subsystem all member ray-sums are sequentially measured during the orbital sweep of the x-ray source 35 in order to generate detector views, or D-views. Because the VT signal (60) and the CE signal (65) trigger detection by the EIDs 25-30 and the PCDs 40-45, respectively, the VT (60) and CE (65) signals set the sampling rates for the respective third and fourth generation CT subsystems. The fourth generation CT subsystem uses a higher sampling rate to determine the D-views than the sampling rate that the third generation CT system uses to generate the S-views. However, both subsystems should be synchronized in order to avoid interference from one system on the other by, for example, having the gantry of the third generation CT subsystem block a view of one of the PCDs 40-45 of the fourth generation CT subsystem while that PCD is carrying out a measurement. This synchronization is accomplished by the timing circuit 20, which generates the VT 60 and CE 65 signals from the signal outputted by the rotational encoder 5.

Figure 2:
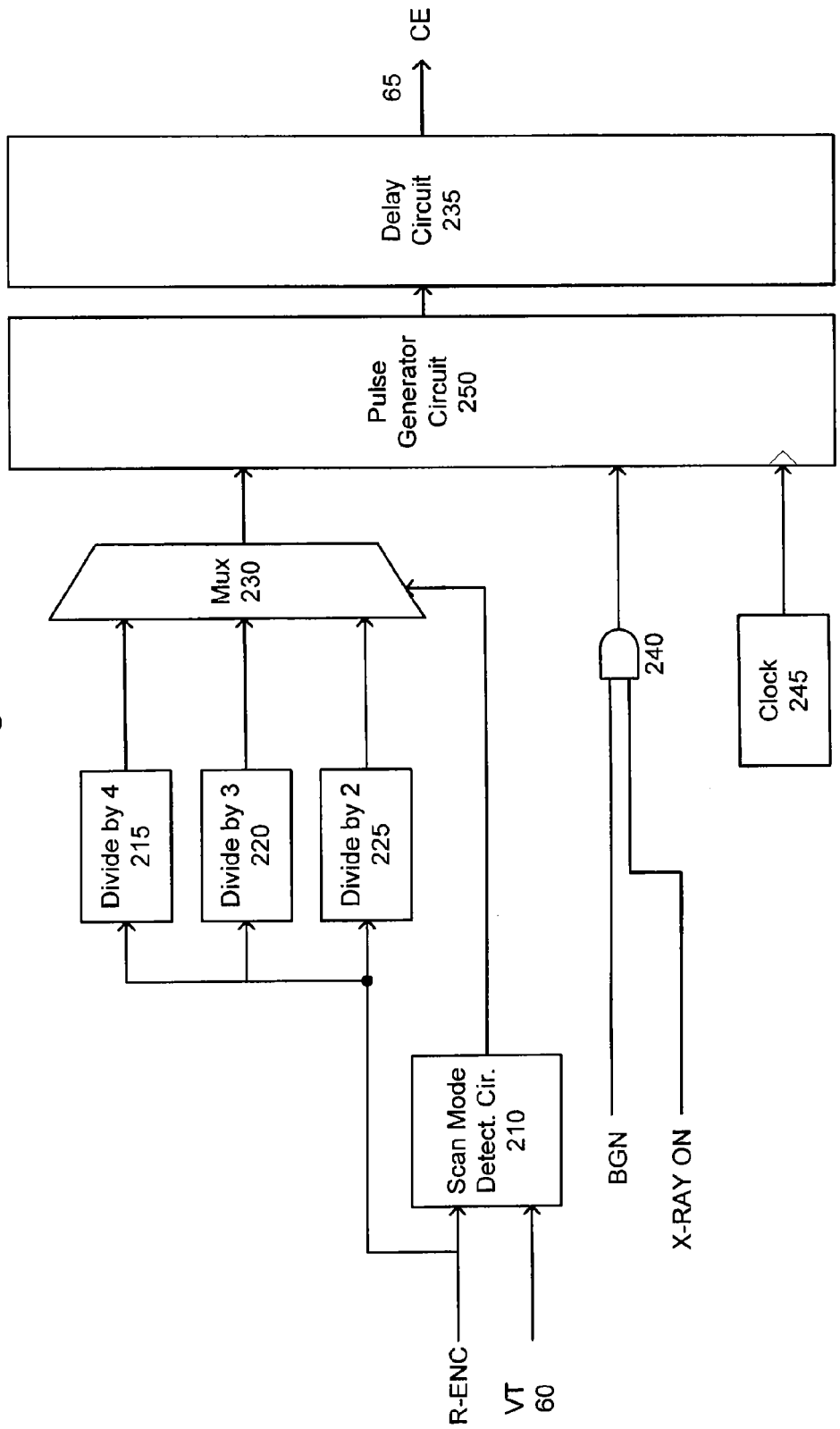
FIG. 2 is a block diagram of a timing circuit according to exemplary embodiments of the present disclosure.

FIG. 2 is a block diagram of aspects of the fourth generation control circuit 15 according to exemplary aspects of the present disclosure. As noted above, the VT signal 60 can be fixed to a predetermined period, such as 833 micro-seconds. The VT signal 60 is to a scan mode detection circuit 210.

The scan mode detection circuit 210 determines the scanning mode of the CT system based on a ratio of the VT signal frequency to the frequency of the rotational encoder signal R-ENC, which is also provided to the scan mode detection circuit 210. As such, the scan mode detection circuit 210 may be a counter that counts the number of R-ENC signal cycles within a period of the VT signal 60. The scan mode detection circuit 210 may also include two times to respectively count a number of cycles of each of the R-ENC and VT signals within a predetermined time period. The result of the counts may then be provided to a dividing circuit or to a microprocessor in order to determine the ratio of R-ENC cycles to VT signal cycles and therefore the scan mode. Thus, the precise implementation of the scan mode detection circuit 210 is not limiting on the present disclosure.

The output of the scan mode detection circuit 210 is used as a control signal to a multiplexer 230 which selects as its output one of three divider circuits 215, 220, and 225. The R-ENC signal is also provided as inputs to the divider circuits 215, 220, 225 which divide this signal by 4, 3 and 2, respectively. Although three divider circuits are shown in FIG. 2 for the sake of simplicity, one of ordinary skill in the art would recognize that more than three dividers may be used or fewer than three dividers may be used without departing from the scope of the present disclosure. Further, the divisors implemented by each divider circuit 215, 220, 225 may be other than 4, 3 and 2, as can be appreciated.

The output of the multiplexer 230 is provided as an input to a pulse generator 250 that generates a pulse in response. The pulse generator circuit 250 also has an edge-triggered clock input to receive a clock signal from a free-running clock source 245. However, non-edge-triggered inputs may also be used without departing from the scope of the present disclosure.

The pulse generator circuit 250 may be enabled or disabled through an enable input to which logic gate 240 is connected. The logic gate 240 receives as inputs the X-RAY ON signal that turns on and off the x-ray source 35 and a "begin" signal (BGN) used to start the generation of the CE signal 65. Although, the logic gate 240 of FIG. 2 is an AND gate, other logic gates, such as OR, XOR, NAND, NOR, etc., may be used, depending on functionality, without departing from the scope of the present disclosure.

The output of the pulse generator circuit 250 is provided to a delay circuit 235, which introduces a delay to this signal in order to generate the CE signal 65. The delay introduced by the delay circuit 235 may be variable or have a fixed value, such as 11 microseconds. The output of this circuit is then provided to the PCDs 40-45.

Figure 3:
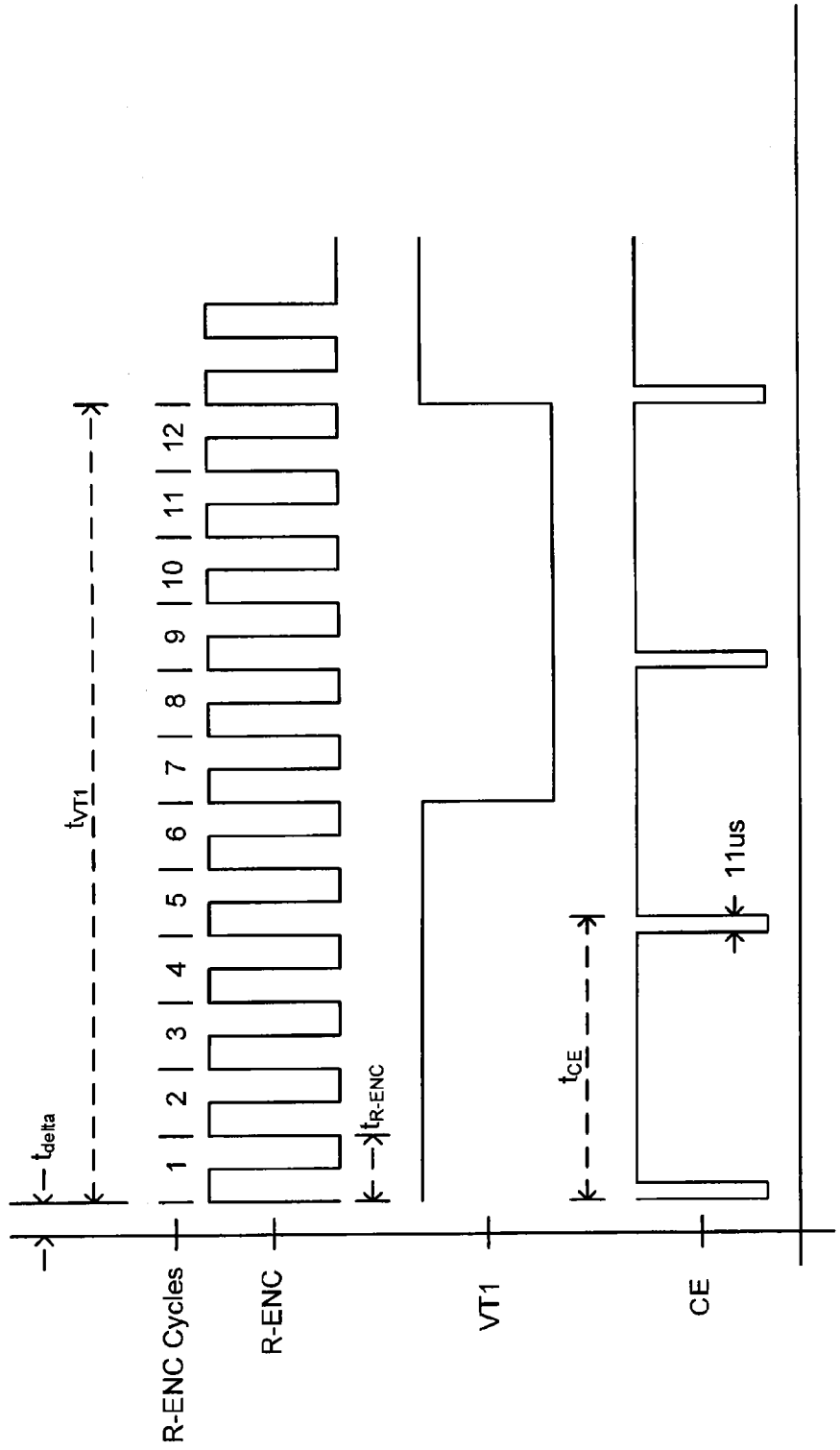
FIG. 3 is a waveform diagram of the signals corresponding to the timing circuit according to exemplary embodiments of the present disclosure.

Next, exemplary functions of fourth generation control circuit 15, and the corresponding signals, are described with reference to FIG. 3. FIG. 3 illustrates a first scan mode in which the ratio of the R-ENC signal period ($t_{R-ENC}$) to the VT signal period ($t_{VT1}$) is twelve. That is, the R-ENC signal cycles twelve times within a single period of the VT signal 60. In this scan mode, the scan mode detector 210 outputs a value to the multiplexer 230 such that the multiplexer 230 selects the divider 215 as its output. The output of the multiplexer 230 is the CE signal prior to the addition of the delay by the delay circuit 235. In this case, since the R-ENC signal is divided by 4 by divider circuit 215, the period of the CE signal ($t_{CEN}$) is four times that of the R-ENC signal.

The delay circuit 235 then introduces a delay (11 microseconds) into the divided R-ENC signal which is then outputted therefrom as the CE signal 65. Note that a small lag ($t_{delta}$) may be present as the begin signal (BGN) and X-RAY ON signal cause the pulse generator circuit 250 to be enabled and/or as the system starts for the first time (i.e., as a result of power-up.)

In FIG. 3, the R-ENC, VT and CE signals are illustrated as square-wave signals. However, one of ordinary skill would recognize that the R-ENC, VT and CE signal may also be saw-tooth, triangular or sinusoidal, and may be base-band or modulated by a carrier frequency. Further, these signals may be offset by a direct current (DC) voltage or may be symmetrical about the zero-volt axis. As such, the precise waveform of the R-ENC, VT and CE signals is not limiting on the present disclosure.

Figure 4:
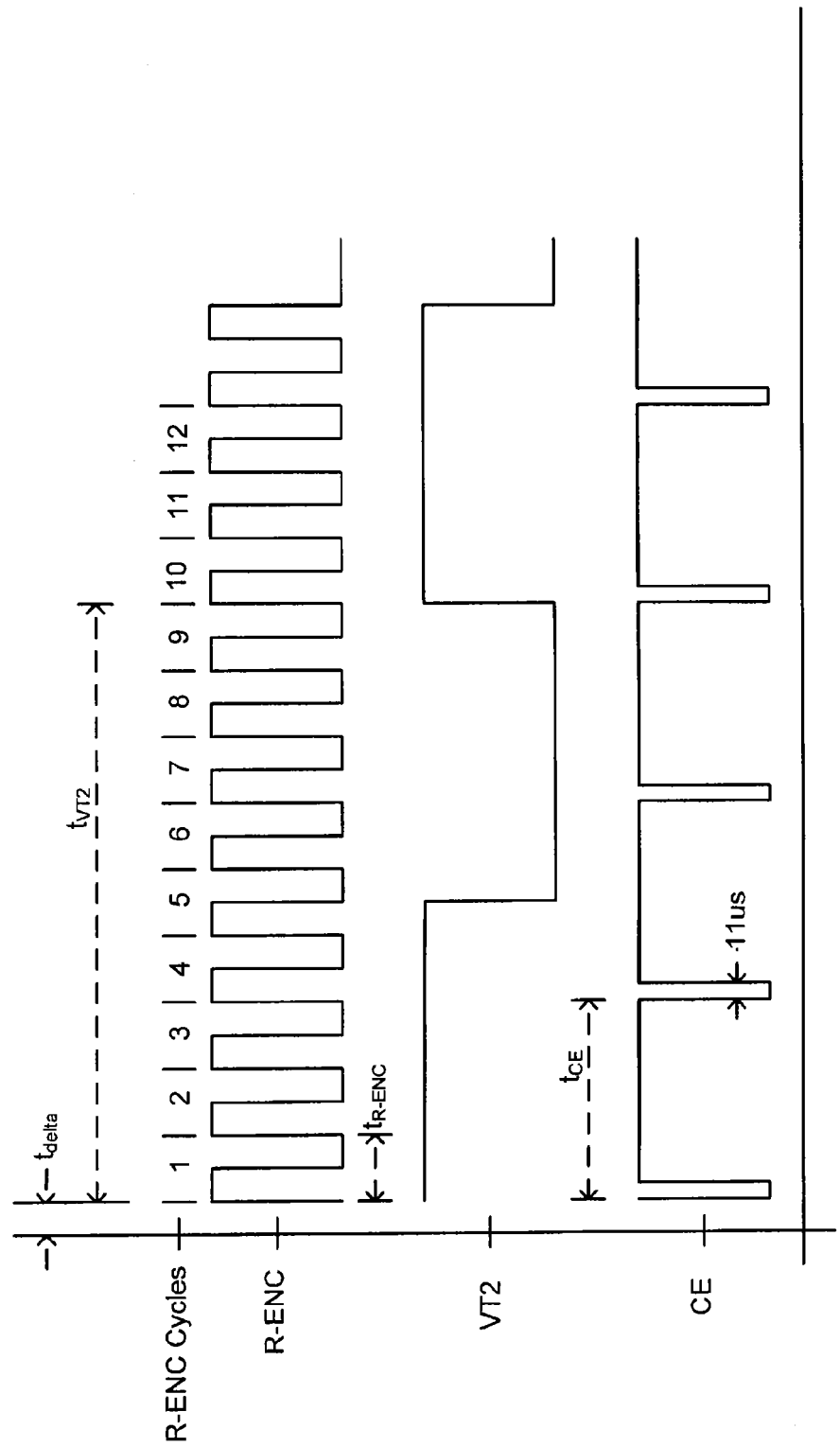
FIG. 4 is another waveform diagram of the signals corresponding to the timing circuit according to exemplary embodiments of the present disclosure.

FIG. 4 is a diagram of the R-ENC, VT and CE signals during a second scan mode of the CT system. In FIG. 4 the ration of the R-ENC signal period ($T_{R-ENC}$) to the VT signal period ($t_{VT2}$) is nine. Based on this value, the scan mode detection circuit 210 generates a signal to cause the multiplexer 230 to choose the output of the divider circuit 220 as its output. In this case, the R-ENC signal is divided by 3 in the divider circuit 220 to generate a divided R-ENC.

The divided R-ENC signal is then provided to the pulse generator circuit 250 by the multiplexer 230, the output of which is provided to the delay circuit 235, which introduces an 11 micro-second delay into this signal to generate the CE signal 65. In FIG. 4 there are fewer cycles of the R-ENC signal within a period ($t_{CE}$) of the CE signal than in FIG. 3. However, the number of cycles of the CE signal relative to the number of cycles of the VT signal is the same for both FIGS. 3 and 4 (i.e., for scan modes 1 and 2). As such, the VT and CE signals remain both frequency and phase locked relative to each other. As discussed above, the waveform of the R-ENC, VT and CE signals does not limit the scope of this disclosure.

Figure 5:
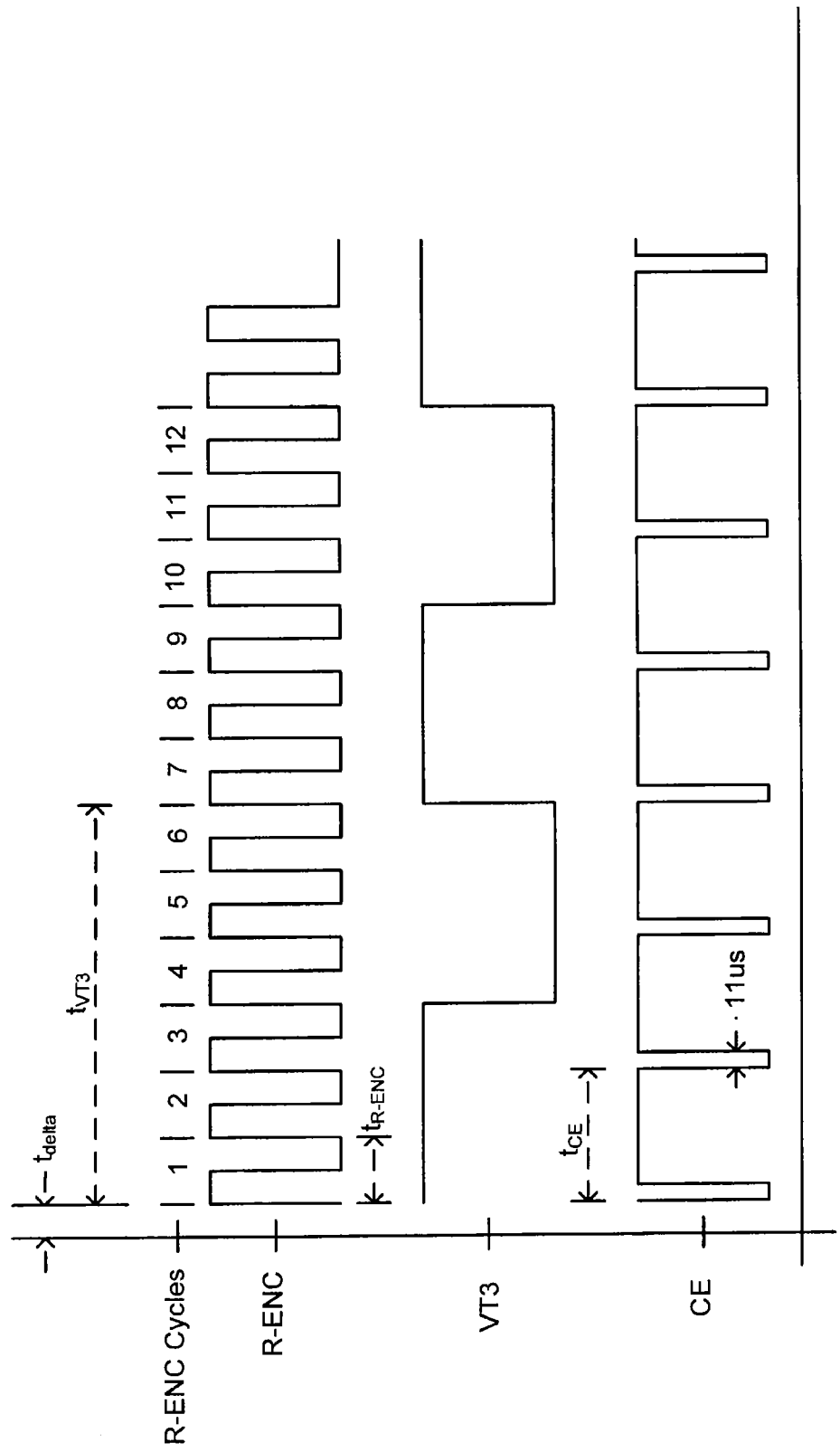
FIG. 5 is a further waveform diagram of the signals corresponding to the timing circuit according to exemplary embodiments of the present disclosure.

FIG. 5 is a diagram of the R-ENC, VT and CE signals during a third scan mode. In FIG. 5, the ratio of the period of the R-ENC signal ($t_{R-ENC}$) to the period of the VT signal ($t_{VT3}$) is 6. Based on this ratio, the scan mode detection circuit 210 outputs a control signal to the multiplexer 230 such that the multiplexer selects as its output the output of the divider circuit 225. The divider circuit 225 divides the R-ENC signal by 2 to generate a divided R-ENC signal. The divided R-ENC signal is provided to the pulse generator circuit 250, whose output is then delayed by, for example, 11 microseconds by the delay circuit 235. The resulting output is outputted as the CE signal 65. As in the case of the first and second scan modes, the CE signal remains frequency and phase locked with the VT signal even though the period ratio between the VT and R-ENC signals and between the CE and R-ENC signals have changed. As noted previously, the waveform of these signals is not limiting upon the present disclosure.

Figure 6:
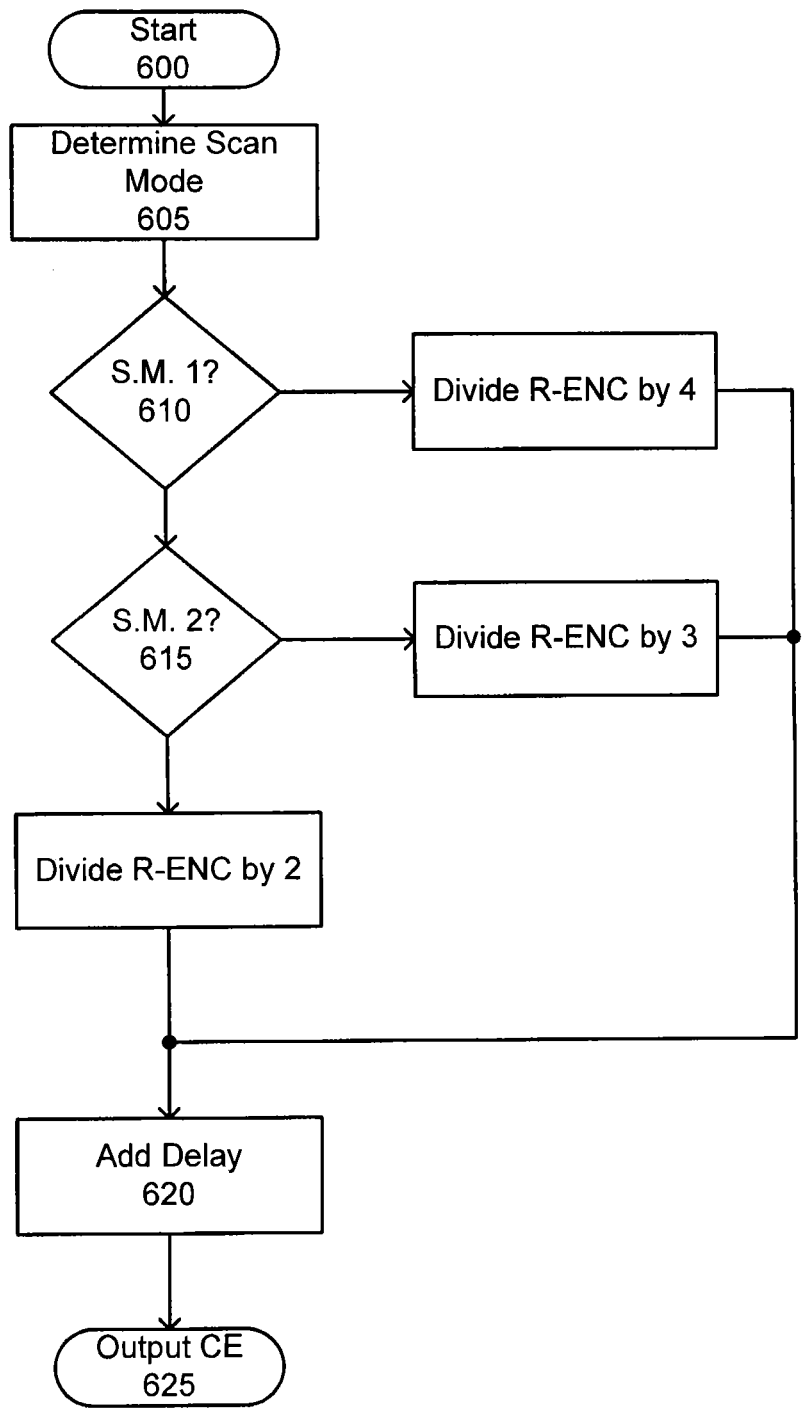
FIG. 6 is a flow chart according to exemplary embodiments of the present disclosure.

Next the process performed by an exemplary system, such as that of FIG. 1 is explained with reference to FIG. 6. In FIG. 6, the process begins at step 600 and proceeds to step 605 where the scan mode detection circuit 210 determines the scan mode based on a ratio of the periods of the R-ENC and VT signals, as discussed above. At step 610, the process determines whether the CT system is in the first scan mode. If the CT system is in the first scan mode, the process moves to step 630 where the R-ENC signal is divided by 4 to generate a divided R-ENC signal, which causes the pulse generator circuit 250 to output a corresponding pulse. Then the process moves to step 620 where the delay circuit 235 adds a predetermined delay, such as 11 micro-seconds, to output of the pulse generator circuit 250 in order to generate the CE signal, which is output at step 625 where the process ends.

If at step 610 it is determined that the CT system is not in the first scan mode, the process moves to step 615 where it is determined whether the CT system is in the second scan mode. If it is, the process moves to step 635 where the R-ENC signal is divided by 3, which causes the pulse generator circuit 250 to generate a corresponding pulse. Then the process moves to step 620 where the delay circuit 235 adds the delay as described above to generate the CE signal. At step 625 the CE signal is output and the process ends.

If at step 615, it is determined that the CT system is not in the second mode, the system assumes that the CT system is in the third mode and proceeds to step 640 where the R-ENC signal is divided by 2 and the corresponding pulse from the pulse generator circuit 250 is then provided to the delay circuit, which introduces the delay at step 620 to generate the CE signal. At step 625 the CE signal is output and the process ends.

Any processes, descriptions or blocks in flow charts should be understood as representing modules, segments, portions of code which include one or more executable instructions for implementing specific logical functions or steps in the process, and alternate implementations are included within the scope of the exemplary embodiment of the present invention in which functions may be executed out of order from that shown or discussed, including substantially concurrently or in reverse order, depending upon the functionality involved, as would be understood by those skilled in the art. Further, it is understood that any of these processes may be implemented as computer-readable instructions stored on computer-readable media for execution by a processor.

While certain embodiments have been described, these embodiments have been presented by way of example only, and are not intended to limit the scope of the inventions. Indeed, the novel apparatus, methods and systems described herein may be embodied in a variety of other forms. Furthermore, various omissions, substitutions and changes in the form of the apparatus, methods and systems described herein may be made without departing from the spirit of the inventions. The accompanying claims and their equivalents are intended to cover such forms or modifications as would fall within the scope and spirit of the inventions.

The invention claimed is:

1. A control circuit for a computer-aided tomography (CT) system, comprising:
    a first input to receive a master timing signal;
    a second input to receive a first timing signal
    a mode detection circuit configured to determine a scan mode of the CT system based on the master timing signal and the first timing signal, the first timing signal having a lower frequency than a frequency of the master timing signal; and
    a timing circuit configured to generate a second timing signal based on the master timing signal and the scan mode of the CT system, the second timing signal having a lower frequency than the frequency of the master timing signal and a higher frequency than the frequency of the first timing signal.

2. The control circuit according to claim 1, wherein the first timing signal, the second timing signal, and the master timing signal remain phase-locked irrespective of the scan mode.

3. The control circuit according to claim 2, wherein the control circuit includes:
    a first divider circuit configured to divide the master timing signal by a first predetermined value;
    a second divider circuit configured to divide the master timing signal by a second predetermined value;
    a third divider circuit configured to divide the master timing signal by a third predetermined value; and
    a multiplexer configured to output an output of one of the first, second or third divider circuit based on the scan mode.

4. The control circuit according to claim 3, wherein the scan mode detection circuit is configured to detect the scan mode based on a ratio of a period of the master timing signal to a period of the first timing signal.

5. The control circuit according to claim 4, wherein the period of the master timing signal is an integer multiple of the period of the first timing signal.

6. The control circuit according to claim 3, wherein the control circuit further includes
    a pulse generator circuit configured to generate a pulse signal based on the output of the multiplexer, and
    a delay circuit configured to delay an output of the pulse generator by a predetermined time interval to generate the second timing signal.

7. The control circuit according to claim 1, wherein the master timing signal is generated as a rotational encoder signal of a rotational CT gantry by a rotational encoder circuit, the first timing signal is derived from the master timing signal and provided as a view trigger to a first CT subsystem, and the control circuit provides the second timing signal as a count enable signal to a second CT subsystem.

8. A computer-aided tomography (CT) system, comprising:
a first CT subsystem including
a gantry encoder configured to generate a rotational encoder signal based on rotation of a rotational gantry, and
a control circuit configured to capture first CT images based on a view trigger signal that has a frequency lower than a frequency of the rotational encoder signal;
a second CT subsystem including a control circuit configured to capture second CT images based on a count enable signal, the control circuit of the second CT subsystem being configured to
determine a scan mode of the CT system based on a ratio of a period of the rotational encoder signal to a period of the view trigger signal, and
generate the count enable signal based on the rotational encoder signal and the scan mode, the count enable signal having a frequency higher than the frequency of the view trigger signal and lower than the frequency of the rotational encoder signal.

9. The CT system according to claim 8, wherein the first CT subsystem further includes:
at least one x-ray source configured to generate x-rays and mounted on the rotational gantry, and
at least one energy integrating detector configured to measure x-rays from the at least one x-ray source, the at least one energy integrating detector being mounted on the rotational gantry.

10. The CT system according to claim 9, wherein the second CT subsystem includes:
at least one fixed photon counting detector configured to count photons corresponding to the x-rays received from the at least one x-ray source, the at least one fixed photon detector being fixed at a predetermined radius with respect to the central axis.

11. The CT system according to claim 10, wherein the rotational gantry of the first CT subsystem is configured to rotate about the central axis.

12. The CT system according to claim 11, wherein the first CT subsystem is a third generation CT system and the second CT subsystem is a fourth generation CT system.

13. The CT system according to claim 8, wherein control circuit of the second CT subsystem maintains the view trigger signal and the count enable signal phase-locked irrespective of the scan mode of the CT system.

14. The CT system according to claim 13, wherein the control circuit of the second CT subsystem maintains the view trigger signal and the count enable signal frequency-locked irrespective of the scan mode of the CT system.

15. The CT system according to claim 8, wherein the control circuit of the second CT subsystem further includes:
a first divider circuit configured to divide the rotational encoder signal by a first predetermined value;
a second divider circuit configured to divide the rotational encoder signal by a second predetermined value;
a third divider circuit configured to divide the rotational encoder signal by a third predetermined value; and
a multiplexer configured to output an output of one of the first, second or third divider circuit based on the scan mode.

16. The CT system according to claim 15, wherein the control circuit of the second CT subsystem further includes:
a pulse generator circuit configured to generate a pulse signal based on the output of the multiplexer, and
a delay circuit configured to delay an output of the pulse generator circuit by a predetermined time interval to generate the count enable signal.

17. The CT system according to claim 8, further comprising:
a reference detector configured to output a reference signal to the first CT subsystem based on the view trigger signal, the reference signal being used by the first CT subsystem to normalize captured image data.

18. The CT system according to claim 15, wherein the period of the rotational encoder signal is an integer multiple of the period of the view trigger signal.

19. A method of synchronizing a computer-aided tomography (CT) system, comprising:
generating, in a rotational encoder, a rotational encoder signal based on rotation of a rotational gantry of a first CT subsystem;
determining, in a scan mode detection circuit, a scan mode of the CT system based on the rotational encoder signal and a view trigger signal of the first CT subsystem, the view trigger signal having a lower frequency than a frequency of the rotational encoder signal;
capturing, in the first CT subsystem, first CT images based on the view trigger signal;
generating, in a control circuit, a count enable signal based on the rotational encoder signal and the scan mode, the count enable signal having a frequency higher than the frequency of the view trigger signal and lower than a frequency of the rotational encoder signal; and
capturing second CT images in a second CT subsystem based on the count enable signal.

20. A non-transitory computer-readable medium encoded with computer readable instructions that, when executed by a computer, cause the computer to perform a method comprising:
generating a rotational encoder signal based on rotation of a rotational gantry of a first CT subsystem;
determining a scan mode of the CT system based on the rotational encoder signal and a view trigger signal of the first CT subsystem, the view trigger signal having a lower frequency than a frequency of the rotational encoder signal;
capturing first CT images based on the view trigger signal;
generating a count enable signal based on the rotational encoder signal and the scan mode, the count enable signal having a frequency higher than the frequency of the view trigger signal and lower than a frequency of the rotational encoder signal; and
capturing second CT images based on the count enable signal.

* * * * *